United States Patent [19]

Nebolon

[11] Patent Number: 5,409,449
[45] Date of Patent: Apr. 25, 1995

[54] DETENT MECHANISM FOR A HINGED ORTHOPEDIC BRACE

[75] Inventor: Joseph F. Nebolon, Del Mar, Calif.

[73] Assignee: Smith & Nephew Donjoy Inc., Carlsbad, Calif.

[21] Appl. No.: 89,017

[22] Filed: Jul. 9, 1993

[51] Int. Cl.⁶ ............................................. A61F 5/00
[52] U.S. Cl. ........................................ 602/16; 602/26; 403/107; 403/104; 16/333
[58] Field of Search .................. 602/5, 16, 26, 20, 23; 16/324, 333, 334; 403/107, 106, 104, 103, 97, 98, 95

[56] References Cited

U.S. PATENT DOCUMENTS

| | | |
|---|---|---|
| 401,933 | 4/1889 | DeCamp . |
| 2,911,245 | 11/1959 | Kurz ........................................ 403/95 |
| 3,352,580 | 11/1967 | Kurz et al. ........................ 403/107 X |
| 3,902,482 | 9/1975 | Taylor . |
| 4,054,130 | 10/1977 | Franke . |
| 4,340,041 | 7/1982 | Frank . |
| 4,397,308 | 8/1983 | Hepburn . |
| 4,456,003 | 6/1984 | Allard et al. ........................... 602/16 |
| 4,481,941 | 11/1984 | Rolfes . |
| 4,489,718 | 12/1984 | Martin . |
| 4,531,515 | 6/1985 | Rolfes . |
| 4,599,998 | 7/1986 | Castillo . |
| 4,890,607 | 1/1990 | Townsend ............................... 602/26 |
| 4,929,113 | 5/1990 | Sheu ..................................... 403/325 X |
| 4,955,369 | 9/1990 | Bledsoe et al. . |
| 4,982,732 | 1/1991 | Morris . |
| 5,000,169 | 3/1991 | Swicegood et al. . |
| 5,002,044 | 3/1991 | Carter . |
| 5,062,858 | 11/1991 | Broeck et al. . |
| 5,078,127 | 1/1992 | Daneman et al. . |
| 5,188,584 | 2/1993 | Petrofsky et al. ................ 602/26 X |
| 5,230,676 | 7/1993 | Silver et al. ........................ 602/26 X |

FOREIGN PATENT DOCUMENTS

2215213 9/1989 United Kingdom ................. 602/16

Primary Examiner—Richard J. Apley
Assistant Examiner—Linda C. M. Dvorak
Attorney, Agent, or Firm—Rodney F. Brown

[57] ABSTRACT

A hinge assembly is provided for an orthopedic brace having a rotatable hinge and a detent mechanism to automatically, yet releasably, lock the hinge in a fixed position of rotation. The hinge includes two rotatably attached members and the detent mechanism includes an indentation formed in the attached end of one member and a block pivotally mounted on the other member. The block has a locking projection that is biased toward the indentation and cooperates therewith to provide three positions of operation, a locked position, a release position, and an activated position. In the locked position, the locking projection fittingly engages the indentation, thereby substantially preventing rotation of the hinge. The release position displaces the locking projection a radial distance away from the indentation, thereby permitting the hinge to rotate freely. In the activated position, the block disengages the indentation and maintains an angular distance therefrom so that the detent mechanism does not obstruct rotation of the hinge, but enables automatic repositioning of the hinge assembly to the locked position whenever the locking projection and indentation angularly realign.

27 Claims, 3 Drawing Sheets

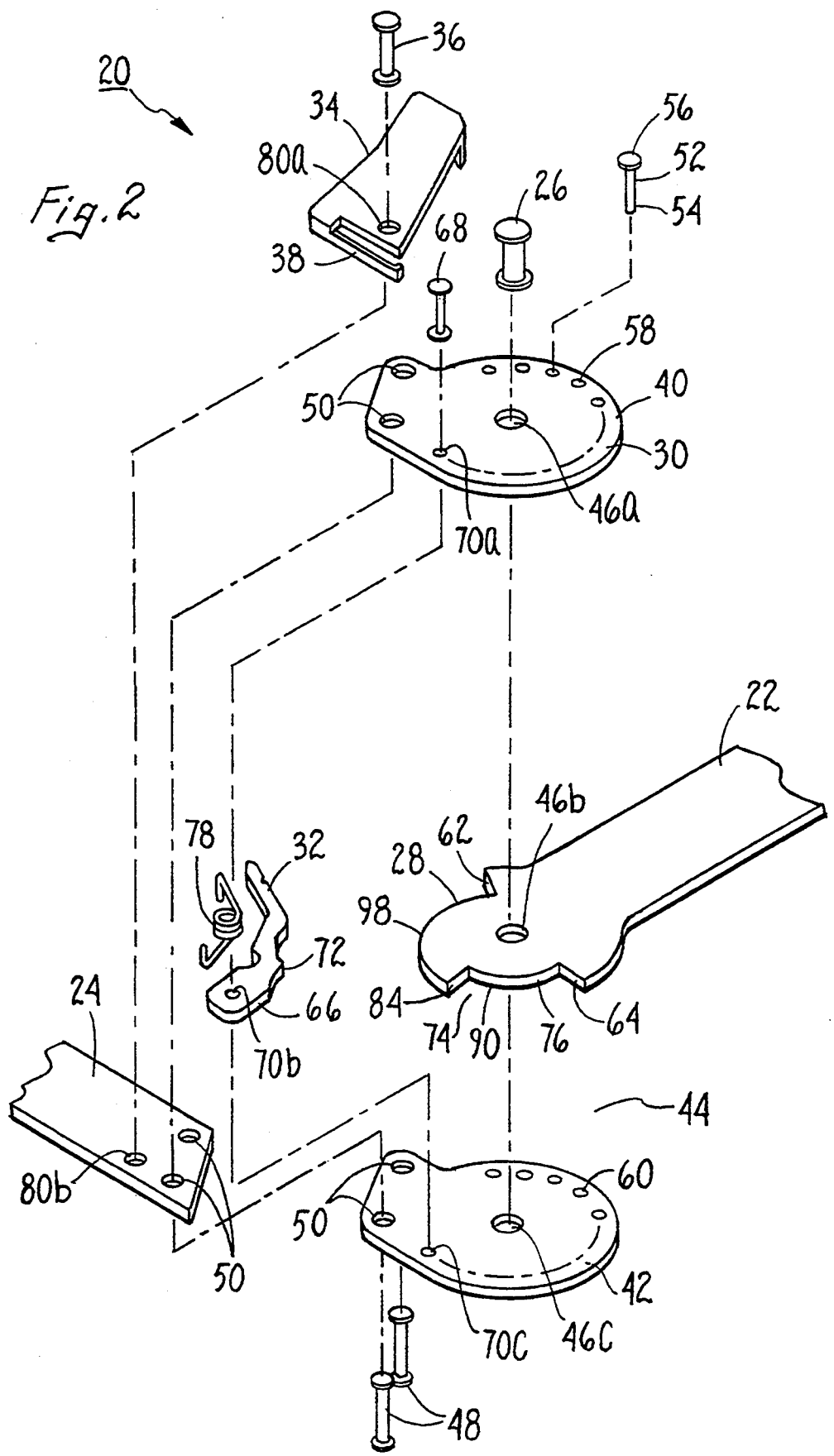

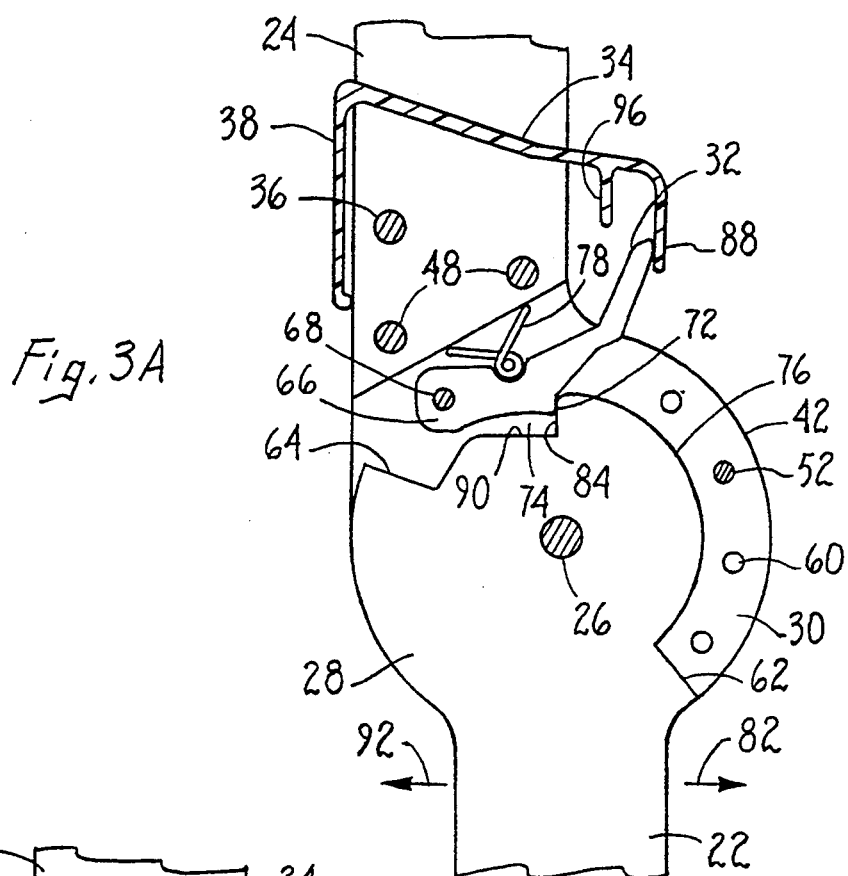
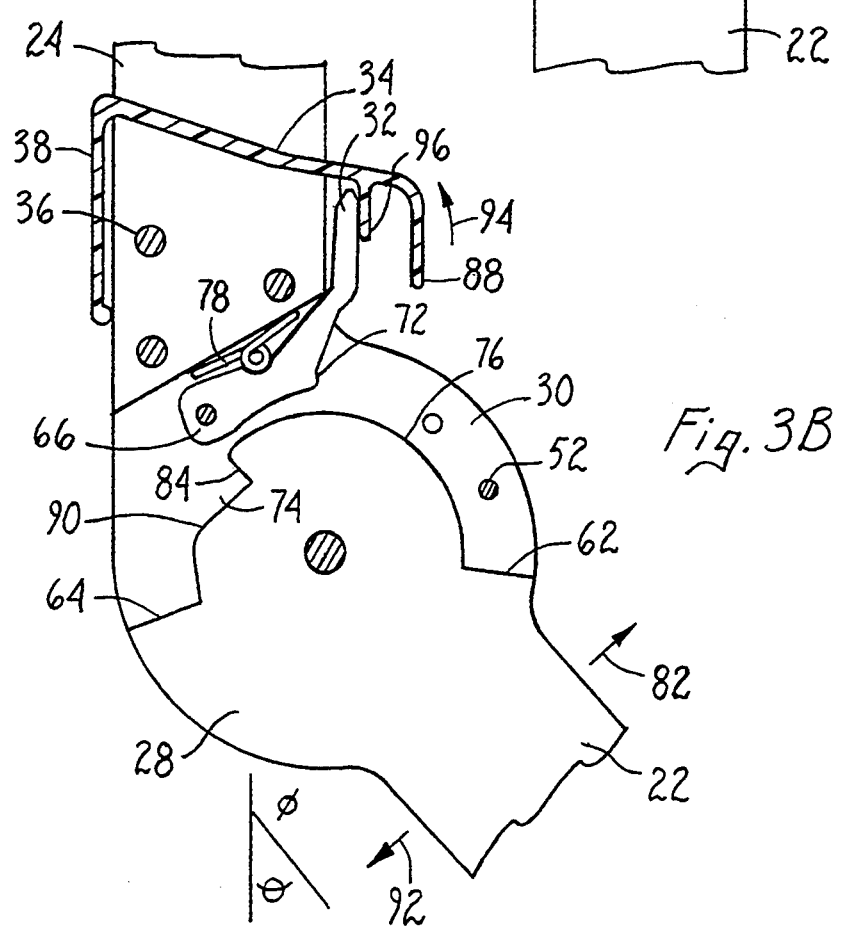

DETENT MECHANISM FOR A HINGED ORTHOPEDIC BRACE

TECHNICAL FIELD

The present invention relates generally to orthopedic braces, particularly to an orthopedic brace having a rotatable hinge, and more particularly to a detent mechanism for releasably locking a hinged orthopedic brace in a fixed position.

BACKGROUND OF THE INVENTION

Hinged orthopedic braces having an adjustable range of hinge rotation, as disclosed by U.S. Pat. Nos. 4,481,941 and 4,531,515, both to Rolfes, are known in the art. The braces disclosed therein have selectively positionable pins placed in predetermined holes about the hinge to act as stops limiting the range of hinge rotation and corresponding joint motion in accordance with the needs of the user. For example, it is oftentimes desirable to strictly limit the range of joint motion available to a patient immediately following surgery by limiting the range of hinge rotation that a brace positioned about the joint permits. The braces disclosed by the above-referenced patents are generally effective for this purpose.

Although a limited degree of hinge rotation and corresponding joint motion can be desirable during rehabilitation of the joint, there are situations where it is advantageous to lock the hinge in a fixed position of rotation. For example, hinge rotation can be desirable when the patient is undergoing a controlled exercise regimen or when the patient is relaxing. Yet, the hinge is preferably maintained in a locked position when the patient initially resumes unsupervised activities, such as walking, to avoid reinjury to the joint before it is fully rehabilitated.

As such, it is an object of the present invention to provide a hinge assembly for an orthopedic brace that enables a range of joint motion in one mode of operation and locks the joint into a fixed position in another mode of operation. It is another object of the present invention to provide such a hinge assembly that is operationally simple, requiring a minimum of user dexterity, skill and know-how. It is yet another object of the present invention to provide such a hinge assembly that readily transitions between the dynamic and static modes of operation with a minimal degree of user intervention. It is a further object of the present invention to provide such a hinge assembly that resists undesirable accidental repositioning of the assembly between the modes of operation.

SUMMARY OF THE INVENTION

The present invention is a hinge assembly for an orthopedic brace positionable about a joint to stabilize and support the joint. The hinge assembly has a rotatable hinge and a detent mechanism to releasably prevent rotation of the hinge in at least one direction. The detent mechanism is preferably configured to prevent rotation of the hinge and corresponding joint in the flexion direction when the hinge and joint are in a full extension position.

The rotatable hinge includes a first elongated member having an end engaging an end of a second elongated member at a point of rotation. The detent mechanism comprises an indentation having a locking face which is formed at the end of the first member on the peripheral edge thereof. The detent mechanism further comprises a block pivotally mounted on the second member at a pivot point proximal to the end of second member. The block has a locking projection that protrudes therefrom and is biased toward the end of the first member by a block biasing spring.

The hinge assembly is adjustably positionable to one of three positions, i.e., a locked position, a release position, or an activated position. The positions of the hinge assembly correspond to radial positions of the locking projection as the block is pivoted about its pivot point, and additionally correspond to angular positions of the hinge as the hinge is rotated about its point of rotation.

In the locked position, the hinge is rotated until the locking projection is in angular alignment with the indentation, enabling the locking projection to radially pivot into the indentation under the force of the block biasing spring. The locking projection is configured to fittingly engage the indentation in abutment with the locking face, thereby substantially preventing rotation of the second member in the direction of the locking face.

The indentation is preferably positioned on the first member such that angular alignment with the locking projection occurs when the hinge is rotated to full joint extension. Correspondingly, the locking face is preferably aligned to face away from the direction of flexion rotation of the first member. Thus, flexion rotation of the hinge from full joint extension is substantially impeded when the locking projection abuts the locking face.

A release force counteracting the force of the block biasing spring is required to disengage the locking projection and indentation when the assembly is in the release position. The release force displaces the locking projection a radial distance away from the position it occupies when the assembly is in the locked position. The locking projection, and preferably the remainder of the block as well, is maintained radially clear of the second member in the release position, thereby permitting the hinge to rotate free of the detent mechanism.

Unlike the locked position and the activated position described hereafter, the release position is solely dependent on the relative radial positions of the indentation and the locking projection. The release position is maintainable independent of the relative angular positions of the indentation and locking projection, whereas the indentation and locking projection must be angularly aligned to achieve the locked position and must be angularly unaligned to achieve the activated position.

In the activated position, the hinge is rotated such that the block, including the locking projection, engages a relatively smooth segment of the peripheral edge an angular distance away from the indentation, while disengaged from the indentation. Although the block biasing spring biases the block radially against the edge in the activated position, the smooth surface of the segment enables slidable engagement of the block thereagainst. Accordingly, when the assembly is in the activated position, the detent mechanism does not obstruct rotation of the hinge.

The present invention desirably enables automatic repositioning of the hinge assembly from the activated position to the locked position without operator intervention. The force of the block biasing spring automatically displaces the locking projection into the cooperatively configured indentation whenever the locking projection and indentation angularly align while the assembly is in the activated position. Conversely, the spring force and detent mechanism configuration desirably restrict unintentional repositioning of the assembly from the locked position to the release or activated position unless an external release force is intentionally applied to the block.

A displacement arm radially extending from the block clear of the hinge is provided to facilitate application of an external release force to the block. The external release force is typically applied manually to the arm by the user, enabling radial displacement of the locking projection from the indentation, and correspondingly enabling repositioning of the assembly from the locked position to the release position or activated position.

A displacement arm housing is also provided to facilitate retention of the assembly in the locked or release position. The housing pivotally engages the hinge, preferably on the second member, permitting removable positioning of the housing over the arm. Accordingly, manual access to the arm is enabled when the housing is pivoted to an open position and access to the arm is restricted when the housing is pivoted to a closed position. A housing biasing spring engages the hinge and housing to bias the housing in the closed position.

A catch is situated in the housing to engage the displacement arm when the assembly is in the release position. The catch maintains the block and associated arm fixed in the release position, thereby preventing pivoting of the block into the locked or activated position. To reposition the assembly from the release position, the housing and correspondingly the catch are pivoted away from the hinge and displacement arm by a housing displacement force counter to the force of the housing biasing spring. The housing displacement force is preferably applied manually.

If the locking projection is not angularly aligned with the indentation when the housing is pivoted away from the displacement arm, the assembly will automatically reposition into the activated position under the force of the block biasing spring. The assembly, however, will automatically reposition to the locked position, if the locking projection and indentation angularly align.

The housing remains positioned over the displacement arm when the assembly is in the activated and release positions to prevent inadvertent impairment of block pivoting in the activated position or inadvertent release of the block in the locked position. When it is desired to return the assembly to the release position from the locked position, the housing is pivotally removed from over the displacement arm and the block is pivoted into the release position. The housing is then replaced over the displacement arm with the catch in engagement therewith.

The detent mechanism of the present hinge assembly has utility in combination with rotatable hinges generally, as described above. The present detent mechanism has particular utility in combination with a specific rotatable hinge having at least one removable pin to supplementally limit the range of hinge and corresponding joint rotation. The limiting pin effectively defines a limited range of hinge rotation when the detent mechanism is in the release position. The detent mechanism, however, overrides the pin to substantially prevent any hinge rotation when the detent mechanism is in the locked position.

The hinge of the present embodiment has one member with an end configured in the shape of a flat plate extending longitudinally therefrom. The plate has a plurality of spaced-apart holes formed through it in an arranged pattern. The end of the other member is fitted adjacent to the plate and the ends of the two members are rotatably attached by a fastener passing through aligned apertures therein.

The limiting pin is sized to be received by the holes through the plate, the holes being arranged about the fastener. The limiting pin extends through the hole and behind the plate to engage the other member and block further rotation of the hinge in a given direction when the detent mechanism is in the release position. The limiting pin can be selectively placed in a particular hole to establish the desired range of hinge and corresponding joint rotation. When the detent mechanism is repositioned to the locked position via the activated position, rotation of the hinge is prevented, thereby overriding the effect of the limiting pin.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 2 is an exploded perspective view of the hinge assembly of FIG. 1.

FIG. 3A is a cross-sectional view of the hinge assembly of FIG. 1 as seen along line 3—3, wherein the assembly is in the locked position.

FIG. 3B is a cross-sectional view of the hinge assembly of the present invention, wherein the assembly has been repositioned from the locked position of FIG. 3A to the release position.

DESCRIPTION OF PREFERRED EMBODIMENTS

Figure 1:
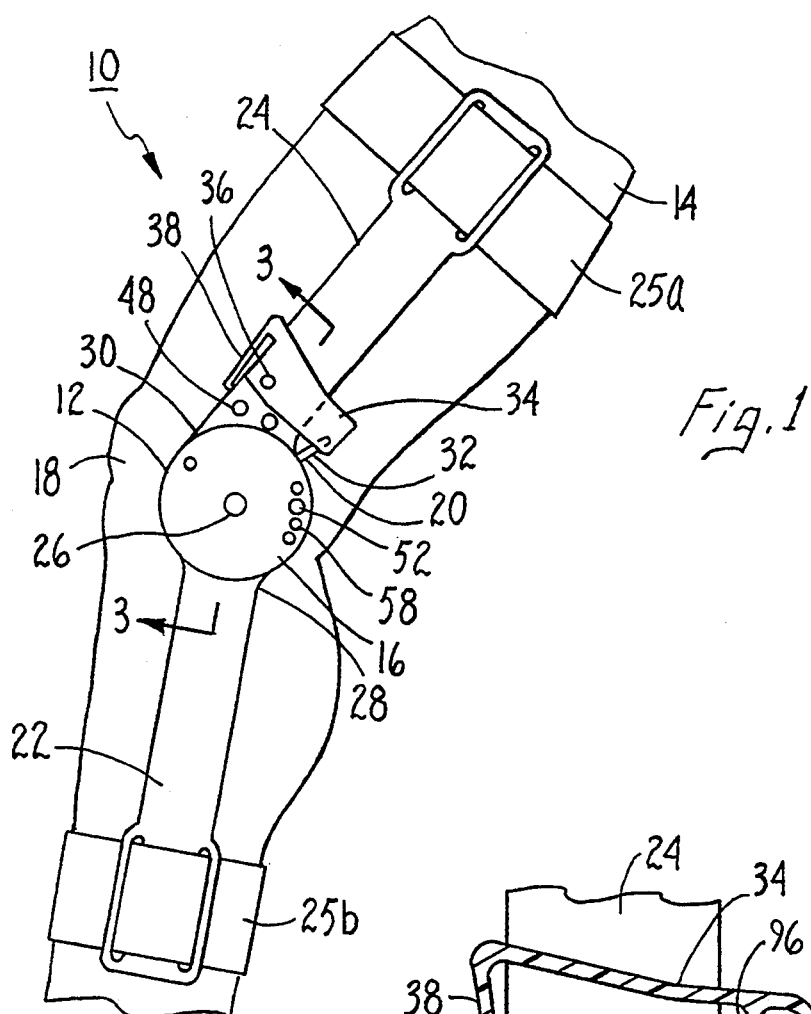
FIG. 1 is a perspective view of an orthopedic knee brace having a hinge assembly of the present invention positioned in place on the leg of a user.

Referring initially to FIG. 1, an orthopedic brace generally designated 10 is shown having a hinge assembly 12 of the present invention. The particular orthopedic brace 10 described by way of example is a post-surgical knee brace fitted to the left leg 14 of a user. It will be apparent to one skilled in the art, however, that the hinge assembly 12 of the present invention can be incorporated into many other types of conventional hinged orthopedic braces applied to the knee, as well as to other joints including the hip, elbow or shoulder, without substantial modification in accordance with the instant teaching.

The hinge assembly 12 includes a rotatable hinge 16 positioned at the knee joint 18 and a detent mechanism 20 adjacent to the hinge 16. A lower pivot bar, termed a first member 22, and an upper pivot bar, termed a second member 24, are substantially rigid support elements for the leg 14. A plurality of straps is provided in engagement with the first and second members 22, 24 to secure the brace to the leg, although only one lower and upper strap 25a, 25b is shown herein with the remainder omitted for clarity. The first and second members 22, 24 are integral components of the hinge 16 insofar as the hinge 16 is created by passing a rivet 26 through the end 28 of the first member 22 and the end 30 of the second member 24, rotatably joining the ends 28, 30.

The detent mechanism 20 includes a displacement arm 32 and a housing 34 removably covering the arm 32. The housing 34 is pivotally attached to the second member 24 by means of a rivet 36 and is biased over the arm 32 by a housing biasing spring 38. Other components of the hinge 16 and detent mechanism 20 shown in FIG. 1 are displayed in greater detail in FIG. 2 (with the straps omitted for clarity), and accordingly are described hereafter with reference thereto.

The specific embodiment of the hinge 16 shown in FIG. 2 has similarities in construction to the hinge disclosed in copending U.S. patent application No. 07/907,480, which is incorporated herein by reference. Accordingly, the end 30 is configured in the form of two substantially parallel plates 40 and 42. A gap 44 is created between the upper first plate 40 and the lower second plate 42. The end 28 fits in the gap 44 where it is rotatably secured to the parallel plates 40, 42 by the rivet 26 passing through the apertures 46a, 46b, 46c. The plates 40, 42 integrally form the end 30 of the second member 24 as a consequence of fixable attachment thereto by means of rivets 48 through apertures 50.

A hinge rotation limiting pin 52 is shown extendable through the first and second plates 40, 42. The limiting pin 52 has an elongated cylindrical body 54 with a widened end 56. A plurality of spaced-apart holes 58 are formed through the first plate 40 in a circumferential pattern. The second plate 42 likewise has a plurality of spaced-apart holes 60 formed therethrough in the same pattern as the first plate 40 such that the holes 58 are alignable with the holes 60.

The body 54 of the limiting pin 52 is smaller in diameter than the holes 58, 60, thereby enabling the holes 58, 60 to receive the limiting pin 52. The widened end 56, however, has a width greater than the diameter of the holes 58, 60 to prevent the limiting pin 52 from passing therethrough. In FIG. 2, the limiting pin 52 is shown to limit flexion rotation of the hinge 16 by abutting a flexion limiting face 62 formed on the end 28, but it is apparent that additional or substitute holes could be provided across the plates 40, 42 to similarly limit extension rotation of the hinge 16 by providing a limiting pin to abut an extension limiting face 64 also formed on the end 28.

In any case, interaction of the limiting pin 52 with the end 28 is incidental to the present invention insofar as operation of the limiting pin 52 is superseded by operation of the detent mechanism 20 when the mechanism 20 is in the locked position as will be shown hereafter. Referring further to FIG. 2, the detent mechanism 20 is shown to include a block 66 pivotally attached to the first and second plates 40, 42 by means of a rivet 68 through apertures 70a, 70b, 70c. The block 66 is preferably a unitary piece of metal machined to the configuration shown.

Integral with the block 66 and extending therefrom are a locking projection 72 and the displacement arm 32. The locking projection 72 is located on the block 66 proximal to the end 28, while the displacement arm 32 is located distal to the end 28 and extends from the block 66 to a position substantially clear of the second member 24. The locking projection 72 is configured to fit within a substantially v-shaped indentation 74 formed in the peripheral edge 76 of the end 28. A block biasing spring 78 is provided to bias the block 66 and associated locking projection 72 in the direction of the end 28. The spring 78 is a conventional torsion spring wedged between the block 66 and the second member 24.

The housing 34 is shown in FIG. 2 to be pivotally attached to the second member 24 by the rivet 36 passing through apertures 80a, 80b. The housing 34 preferably has a molded plastic construction enabling integration of the housing components into a unitary structure. In particular, the housing biasing spring 38 and a pair of catches (not shown in FIG. 2) internal to the housing 34 are preferably integrally formed with the housing 34.

METHOD OF OPERATION

Figure 3C:
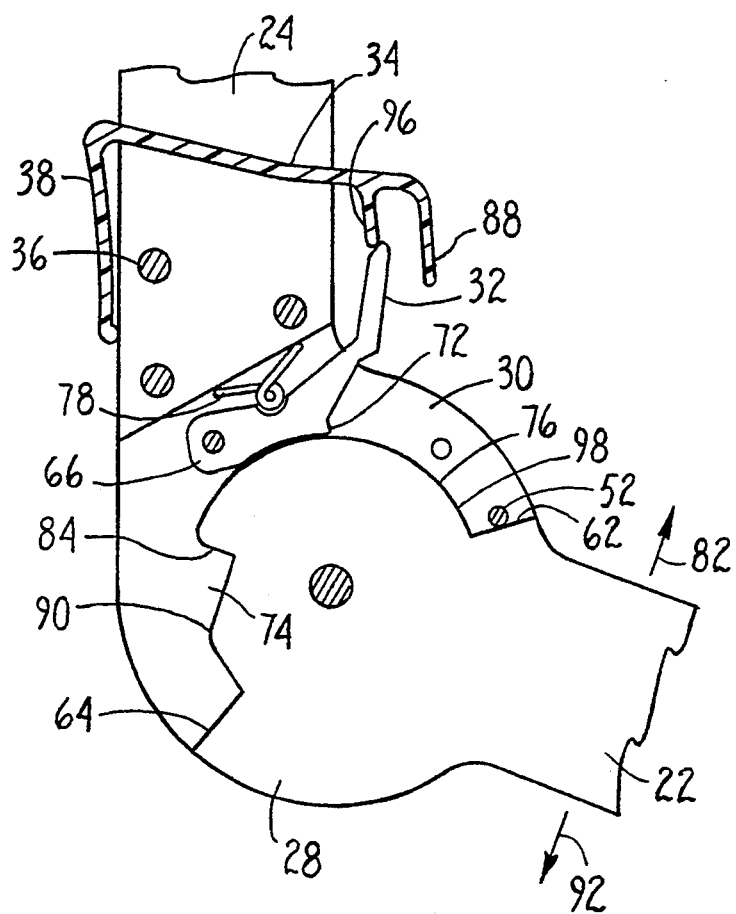
FIG. 3C is a cross-sectional view of the hinge assembly of the present invention, wherein the assembly has been repositioned from the locked position of FIG. 3A to the activated position.

Additional structural features of the present hinge assembly 12 are disclosed hereafter in conjunction with the operation of the assembly 12. The operating positions of the hinge assembly 12 are shown in FIGS. 3A, 3B, and 3C to be a locked position, a release position, and an activated position, respectively. The operating positions of the hinge assembly 12 correspond to radial positions of the block 66 and locking projection 72 as the block 66 is pivoted about the rivet 68, and further correspond to angular positions of the hinge 16 as the hinge 16 is rotated about the rivet 26.

Referring to FIG. 3A, the hinge assembly 12 is in the locked position, wherein the detent mechanism 20 prevents rotation of the hinge 16 in the flexion direction of the first member denoted by an arrow 82 when the hinge 16 is in a full extension position. Full extension is generally achieved when the flexion angle $\theta$ (see FIG. 3B) defined by the relative positions of the members 22, 24 is about 0°. Flexion rotation of the hinge 16 is restricted by angular alignment of the locking projection 72 and indentation 74 and corresponding abutment of the locking projection 72 against a locking face 84 of the substantially v-shaped, albeit asymmetrical, indentation 74.

The biasing force of the block biasing spring 78 has a radial component directed toward the indentation 74 to maintain the locking projection 72 in close fit with the locking face 84 and prevent slippage therefrom. The locking position of the assembly 12 is further secured by engagement of the displacement arm 32 with a locking catch 88 in the housing 34. The biasing force of the housing biasing spring 38 also has a radial component that is directed toward the end 28 to maintain the housing 34 in a closed position and the displacement arm 32 in engagement with the locking catch 88.

The detent mechanism 20 shown herein is configured to prevent hinge rotation in only one direction, i.e., in the direction of flexion 82, by providing only one locking face 84 that is positioned to face away from the direction in which rotation of the first member 22 is restricted. Prevention of hinge rotation in the flexion direction 82 is enabled by the relative steepness of the locking face 84, acting as a catch for the locking projection 72. In contrast, the opposite face 90 of the indentation 74 is relatively shallow enabling substantially unhindered movement of the locking projection 72 therepast in the extension direction denoted by an arrow 92.

It is further apparent to the skilled artisan that prevention of hinge rotation in the extension direction 92 can be provided by reconfiguring the indentation 74 with the locking face on the opposite side thereof. Similarly, restriction of hinge rotation in both directions can be provided by reconfiguring the indentation 74 to a substantially symmetrical v-shape with locking faces on both sides thereof, and correspondingly reconfiguring the locking projection 72.

The cooperative embodiment of the locking projection 72 and indentation 74 shown in FIG. 3A is nevertheless preferred insofar as the embodiment shown therein completely satisfies the desired objective of removably locking the hinge 16 in a position preventing joint flexion. In any case, the extension face 64 on the end 28 would stop against the block 66 before the extension angle $\phi$ (see FIG. 3B) substantially exceeds 180°.

It is noted that the limiting pin 52 is functionally inoperative when the hinge assembly 12 is in the locked position because hinge rotation is locked into a single angular position before the flexion face 62 abuts the pin 52. The limiting pin 52 only becomes operable when the hinge assembly 12 is in the release or activated positions described hereafter with reference to FIGS. 3B and 3C, respectively.

Referring to FIG. 3B, the hinge assembly 12 is in the release position, wherein the detent mechanism 20 does not substantially inhibit rotation of the hinge 16 in either the flexion or extension direction 82, 92. The release position is achieved by manually applying a force counteracting the force of the housing biasing spring 38 to pivot the housing 34 is denoted by an arrow 94. The manual force disengages the displacement arm 32 from the locking catch 88 and exposes the displacement arm 32 to the user.

Once exposed, a manual force having a radial component away from the end 28 is applied to the displacement arm 32 to counteract the force of the block biasing spring 78, thereby pivoting the block 66 about the rivet 68. The arm 32 is correspondingly displaced in substantially the same direction as the arrow 94 and, in doing so, the locking projection 72 is radially displaced clear of the indentation 74. The housing 34 is released thereafter, enabling the release catch 96 to engage the displacement arm 32 and passively maintain the assembly 12 in the release position. As a result, the hinge 16 is rotatable to a plurality of angular positions in either the flexion or extension direction substantially free of the detent mechanism 20.

The limiting pin 52 is provided in the present embodiment to place an adjustable limit on flexion rotation of the hinge 16 when the detent mechanism 20 is in the release position. Thus, the present embodiment of the hinge assembly 12, providing the limiting pin 52 in conjunction with the detent mechanism 20, is desirable where it is advantageous to lock a joint into one fixed angular position in certain situations, while permitting rotation of the joint within a limited range of angular positions in other situations. It is, nevertheless, understood that the hinge assembly 12 disclosed herein remains operable in the absence of supplemental means for limiting the rotation range of the joint, such as the limiting pin 52 disclosed herein, when the assembly 12 is in the release position. In the absence of supplemental rotation limiting means, the hinge 16 simply rotates freely without restriction until the assembly 12 is returned to the locked position.

FIG. 3C shows the hinge assembly 12 in an activated position of operation achieved by manually reapplying a force to the housing 34 counteracting the housing biasing spring 38 to pivot the housing 34 away from the displacement arm 32 and disengage the displacement arm 32 from the release catch 96. The force of the block biasing spring 78 displaces the locking projection 72 in a radial direction against the end 28. The counter force on the housing 34 is withdrawn thereafter, and the housing biasing spring 38 pivotally returns the housing 34 to a partially closed position, wherein the housing biasing spring 38 likewise exerts a biasing force on the displacement arm 32 in the direction of the end 28.

The indentation 74 is preferably angularly displaced away from the locking projection 72 when the projection 72 radially approaches the end 28 such that the projection 72 slidably engages the end 28 along a segment 98 of the peripheral edge 76 away from the indentation 74. The segment 98 is relatively smooth and continuous enabling the hinge 16 to rotate freely within the angular range of slidable engagement between the block 66 and the segment 98. This range is limited in the flexion direction 82 of the first member 22 by the limiting pin 52 and is limited in the extension direction 92 of the first member 22 by the block 66. The hinge 16 is shown in FIG. 3C rotated to the flexion limit occurring when the limiting pin 52 abuts the flexion face 62.

When the hinge assembly is in the activated position, the block 66 is free to pivot about the rivet 68 under the force of the block biasing spring 78 because the displacement arm 32 is substantially clear of both catches 88, 96 and the locking projection 72 is clear of the indentation 74, being a greater radial distance away from the first member 22 relative to the locked position. Thus, the block follows the contour of the segment 98 as the hinge 16 rotates. However, when the hinge 16 is rotated to a point where the locking projection 72 and indentation 74 are angularly aligned, the assembly 12 automatically repositions from the activated position to the locked position of FIG. 3A.

The hinge assembly 12 of the present invention has particular utility where it is desirable to permit some rotation of the hinge 16 in a relaxed flexion position while the user is substantially at rest, but to lock the hinge 16 into a fixed extension position when the user resumes activity, such as when the user transitions from a passive sitting position to an active walking position. Since it is difficult for the user to manually access the assembly 12 while it is adjacent to the knee joint at full extension, the present invention enables the user to set the assembly 12 to the activated position while in flexion. When the user subsequently stands up to full extension, the assembly 12 automatically locks without any further user intervention.

While the forgoing preferred embodiments of the invention have been described and shown, it is understood that alternatives and modifications, such as those suggested and others, may be made thereto and fall within the scope of the invention. Thus, although the above-recited hinge assembly 12 has been shown to include a specific preferred embodiment of the rotatable hinge 16, it is apparent that the present detent mechanism 20 can be readily adapted to cooperate with other known rotatable hinge constructions and such hinge assemblies are within the scope of the present invention. In particular, it is within the purview of the skilled artisan to practice the present invention relying on the detent mechanism to restrict hinge rotation absent the limiting pin, and with or without the cooperation of alternate supplemental means for restricting hinge rotation.

I claim:

1. A hinge assembly for an orthopedic brace having a detent mechanism to releasably prevent rotation of a rotatable hinge in at least one direction, said hinge assembly comprising:

a first member having an end with a peripheral edge and a second member having an end, wherein said end of said first member rotatably engages said end of said second member, thereby providing a rotatable hinge;

an indentation formed in said peripheral edge of said end of said first member; and a block pivotally mounted on said second member at a pivot point and said block having a locking projection positioned thereon, said hinge assembly positionable in a locked position or an activated position as said block is pivoted about said pivot point, wherein engagement of said locking projection and said indentation places said assembly in said locked position such that rotation of said rotatable hinge in at least one direction is substantially prevented, and wherein clearance between said locking projection and said indentation places said assembly in said activated position.

2. A hinge assembly for an orthopedic brace as recited in claim 1, further comprising means for biasing said block toward said first member.

3. A hinge assembly for an orthopedic brace as recited in claim 2, wherein said block biasing means is a block spring engaging said block and said second member.

4. A hinge assembly for an orthopedic brace as recited in claim 1, further comprising a displacement arm extending from said block.

5. A hinge assembly for an orthopedic brace as recited in claim 4, further comprising a displacement arm housing removably covering said displacement arm.

6. A hinge assembly for an orthopedic brace as recited in claim 5, wherein said housing pivotally engages said second member.

7. A hinge assembly for an orthopedic brace as recited in claim 6, further comprising means for biasing said housing over said displacement arm.

8. A hinge assembly for an orthopedic brace as recited in claim 5, wherein said assembly has a release position with said block positioned substantially clear of said first member and further wherein said housing contains means for maintaining said block substantially clear of said first member.

9. A hinge assembly for an orthopedic brace as recited in claim 1, wherein said block slidably engages said peripheral edge away from said indentation when said assembly is in said activated position.

10. A hinge assembly for an orthopedic brace as recited in claim 1, wherein said assembly has a release position with said block positioned substantially clear of said first member and said assembly further comprises means for maintaining said block substantially clear of said first member.

11. A hinge assembly for an orthopedic brace as recited in claim 10, wherein said locking projection is a greater radial distance from said first member when said assembly is in said release position than when said assembly is in said locked position.

12. A hinge assembly for an orthopedic brace as recited in claim 1, wherein said locking projection is a greater radial distance from said first member when said assembly is in said activated position than when said assembly is in said locked position.

13. A hinge assembly for an orthopedic brace as recited in claim 1, wherein said indentation has substantially a v-shape with a first face and a second face, wherein said first face is substantially steeper than said second face.

14. A hinge assembly for an orthopedic brace as recited in claim 13, wherein said first face engages said locking projection when said assembly is in said locked position.

15. A hinge assembly for an orthopedic brace having a detent mechanism to releasably lock a rotatable hinge in an extension position and substantially prevent flexion rotation of the hinge, said hinge assembly comprising:

a first member having an end and a second member having an end, wherein said end of said first member rotatably engages said end of said second member, thereby providing a rotatable hinge;

extension locking means for releasably establishing a locked extension position at a first flexion angle of said first member relative to said second member, said extension locking means comprising an indentation formed in said first member and a block pivotally mounted on said second member at a pivot point and said block having a locking projection positioned thereon, said hinge assembly positionable in said locked extension position or in an activated position as said block is pivoted about said pivot point, wherein engagement of said locking projection and said indentation places said assembly in said locked extension position such that rotation of said rotatable hinge in said flexion direction to increase said first flexion angle is substantially prevented, and wherein clearance between said locking projection and said indentation places said assembly in said activated position.

16. A hinge assembly for an orthopedic brace as recited in claim 15, further comprising flexion limiting means for establishing a flexion limit position at a second flexion angle of said first member relative to said second member, thereby limiting rotation of said first member past said flexion limit position in a flexion direction and preventing an increase in said second flexion angle when said assembly is in said activated position, wherein said second flexion angle is substantially greater than said first flexion angle.

17. A hinge assembly for an orthopedic brace as recited in claim 16, wherein said end of said second member is shaped as a plate, said plate having a plurality of spaced-apart holes formed therethrough, and further wherein said flexion limiting means comprises a pin and a hole through said plate, said pin positioned in said hole to abut said first member at said flexion limit position when said first member is rotated in said flexion direction relative to said second member.

18. A hinge assembly for an orthopedic brace as recited in claim 15, wherein said end of said first member has a peripheral edge and said locking projection slidably engages said peripheral edge away from said indentation when said assembly is in said activated position.

19. A hinge assembly for an orthopedic brace as recited in claim 15, wherein said first flexion angle is about 0°.

20. A hinge assembly for an orthopedic brace having a detent mechanism to releasably prevent rotation of a rotatable hinge in at least one direction, said hinge assembly comprising:

a first member and a second member, wherein said first member rotatably engages said second member, thereby providing a rotatable hinge;

an indentation formed in said first member; and a block pivotally mounted on said second member at a pivot point and said block having a locking projection positioned thereon, said hinge assembly positionable in a locked position or an activated position as said block is pivoted about said pivot point, wherein engagement of said locking projection and said indentation places said assembly in said locked position such that rotation of Said rotatable hinge in at least one direction is substantially prevented, and wherein clearance between said locking projection and said indentation places said assembly in said activated position.

21. A hinge assembly for an orthopedic brace as recited in claim 20, further comprising a displacement arm extending from said block.

22. A hinge assembly for an orthopedic brace as recited in claim 21, further comprising a displacement arm housing removably covering said displacement arm.

23. A hinge assembly for an orthopedic brace as recited in claim 22, wherein said housing pivotally engages said second member.

24. A hinge assembly for an orthopedic brace as recited in claim 22, further comprising means for biasing said housing over said displacement arm.

25. A hinge assembly for an orthopedic brace as recited in claim 22, wherein said assembly has a release position with said block positioned substantially clear of said first member.

26. A hinge assembly for an orthopedic brace as recited in claim 25, wherein said housing contains means for maintaining said block substantially clear of said first member.

27. A hinge assembly for an orthopedic brace as recited in claim 20, wherein said block slidably engages said peripheral edge away from said indentation when said assembly is in said activated position.

* * * * *